United States Patent
Pernicka et al.

(10) Patent No.: US 6,227,665 B1
(45) Date of Patent: May 8, 2001

(54) SPORT EYEGLASSES HAVING REMOVABLE LENSES

(75) Inventors: Martin Pernicka, Laval; Luc Blanchette; Christian Noël, both of Montréal, all of (CA)

(73) Assignee: Leader Industries, Inc., Boucherville (CA)

( * ) Notice: Subject to any disclaimer, the term of this patent is extended or adjusted under 35 U.S.C. 154(b) by 0 days.

(21) Appl. No.: 09/537,975

(22) Filed: Mar. 28, 2000

(30) Foreign Application Priority Data

Oct. 29, 1999 (CA) .................................................. 2287760

(51) Int. Cl.[7] ...................................................... G02C 1/00
(52) U.S. Cl. ................................ 351/86; 351/92; 351/98; 2/445
(58) Field of Search ................................. 351/83, 86, 90, 351/93–95, 98; 2/431, 434, 445

(56) References Cited

U.S. PATENT DOCUMENTS

| | | | |
|---|---|---|---|
| 2,551,144 | * 5/1951 | Lindemann et al. | 351/98 |
| 4,405,214 | 9/1983 | Bolle | 351/88 |
| 4,759,622 | 7/1988 | Schmidthaler | 351/86 |
| 5,069,541 | * 12/1991 | Holmes et al. | 351/86 |
| 5,257,050 | 10/1993 | Wiedner | 351/86 |
| 5,682,621 | 11/1997 | Park | 2/441 |
| 5,790,230 | 8/1998 | Sved | 351/138 |
| 5,802,622 | 9/1998 | Baharad et al. | 2/434 |
| 5,815,235 | * 9/1998 | Runckel | 351/92 |
| 5,963,295 | * 10/1999 | Pernicka | 351/83 |

* cited by examiner

*Primary Examiner*—Huy Mai
(74) *Attorney, Agent, or Firm*—Conley, Rose & Tayon, PC; Eric B. Meyertons

(57) ABSTRACT

Sport eyeglasses having removable lenses formed of a one piece plastic molded frame that includes a pair of lens receiving sections, a pair of opposite strap receiving temple sections and a central bridge section integral with the lens receiving sections are described herein. The bridge section is split to define an upper bridge part and a lower bridge part which are capable of being manually distanced from one another so as to define a gap and allowing lenses to be mounted in the lens receiving sections. A fastening element extends through both bridge parts to secure them together once the lenses are installed in the lens receiving sections.

14 Claims, 2 Drawing Sheets

SPORT EYEGLASSES HAVING REMOVABLE LENSES

FIELD OF THE INVENTION

The present invention generally relates to eyeglasses, especially used for sport activities and so constructed as to allow lenses to be replaced as a result of damages, changes of prescription, shade preference or other reasons.

BACKGROUND OF THE INVENTION

In sport activities, the risk of eyeglasses lenses being damaged is high thereby resulting in the need for a new set of eyeglasses. Additionally, because of the possibility of changes in lens prescription, eyeglasses having the feature of allowing lenses to be easily removed and installed are more and more in demand.

Exchangeable lens eyeglasses to overcome the above described problems have been introduced, see for example, U.S. Pat. No. 4,759,622 issued Jul. 26, 1998 to Schmidthaler and in U.S. Pat. No. 5,682,621 issued Nov. 4, 1997 to Park.

SUMMARY OF THE INVENTION

Disclosed herein are improvements in sport safety glasses to solve the problems of conventional sport glasses in that the lenses may be easily installed to or removed from the eyeglasses frame whenever a user needs to replace them with lenses having a different prescription or shade, or simply to replace a damaged lens.

An embodiment relates to sport eyeglasses having removable lenses which includes a one piece plastic molded frame that includes a pair of lens receiving sections, each having a lens retaining means therein, a pair of opposite temple sections extending to a respective side of the lens receiving sections, and a central bridge section integral with the lens receiving sections. The bridge section is split to define an upper bridge part and a lower bridge part which are capable of being manually distanced from one another to define a gap and to allow lenses to be installed in the lens receiving sections. Means are provided to close the gap and to fixedly retain the lenses in their respective lens receiving sections.

In one embodiment, a fastening element extends through openings in both upper and lower bridge parts and serves to open or close the gap.

In another embodiment, the eyeglasses have integral pins mounted to the rear face of each lens receiving section so that a nose pad may be added to the eyeglasses.

Further objects and scope of protection will be better understood by the detailed description of one embodiment described hereinbelow.

DESCRIPTION OF A PREFERRED EMBODIMENT

Figure 1:
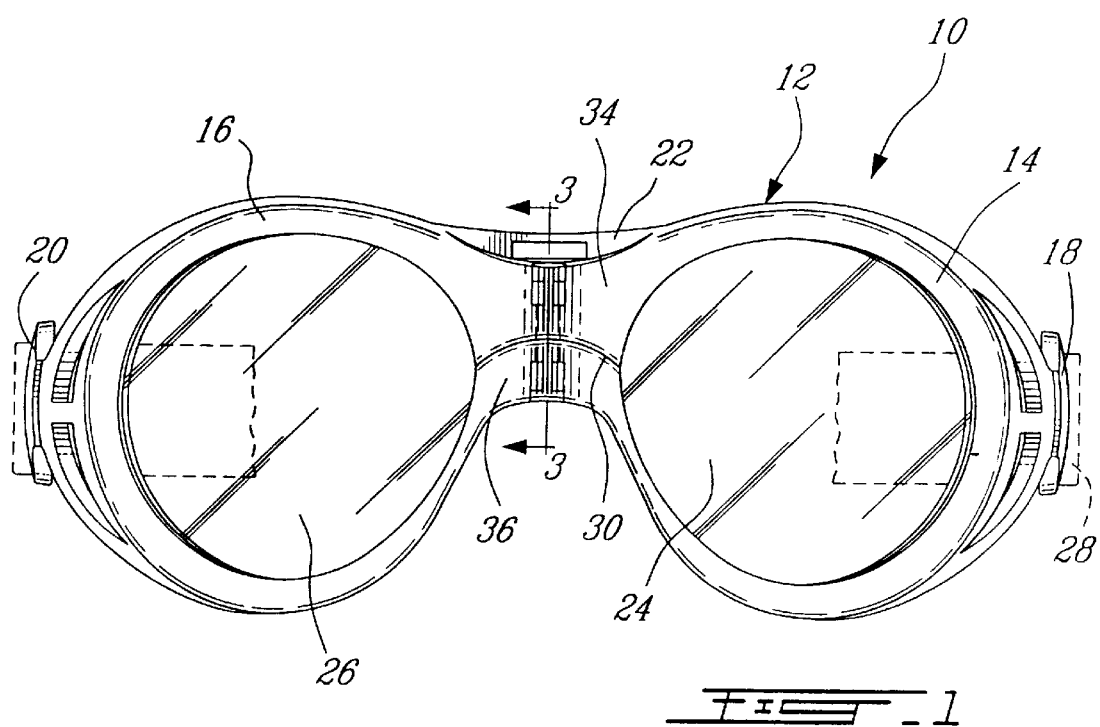
FIG. 1 is a front elevational view of the eyeglasses made in accordance with the present invention.

Referring to the drawings, there is shown a pair of eyeglasses, generally denoted 10, including a one piece plastic molded frame 12 that is formed of various sections including a pair of lens receiving sections 14 and 16, a pair of strap receiving temple sections 18 and 20 and a central bridge section 22.

The lens receiving sections 14 and 16 each have a peripheral rim with an integral inner groove (such as shown as 14a in FIG. 2) into which fits the peripheral edges of a pair of lenses 24 and 26.

The strap receiving temple portions 18 and 20 are equipped, at their respective extremity, to receive means to hold the eyeglasses to a user's head, for example a strap shown in dotted lines as 28.

Figure 2:
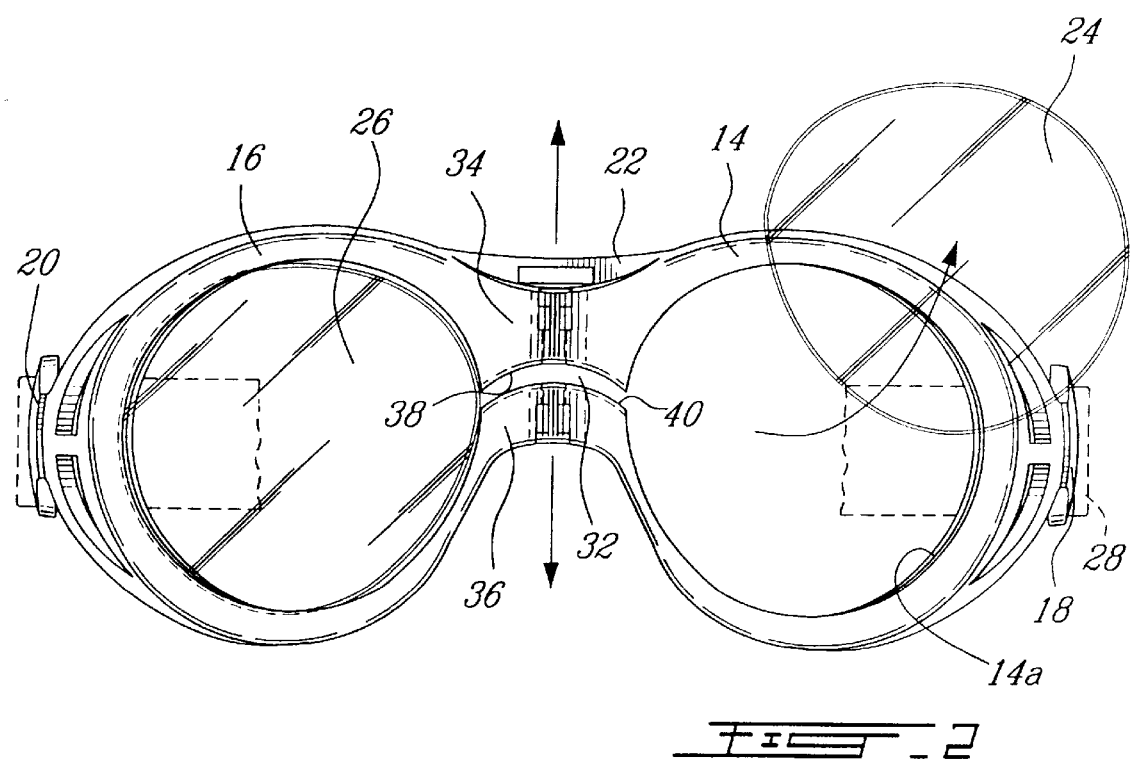
FIG. 2 is a view similar to FIG. 1 showing the eyeglasses in an opened condition allowing the removal of a lens.

The central bridge section 22 is integral with the lens receiving sections and is split at 30 to define a gap 32 (such as shown in FIG. 2) thereby defining an upper bridge part 34 and a lower bridge part 36.

Figure 3:
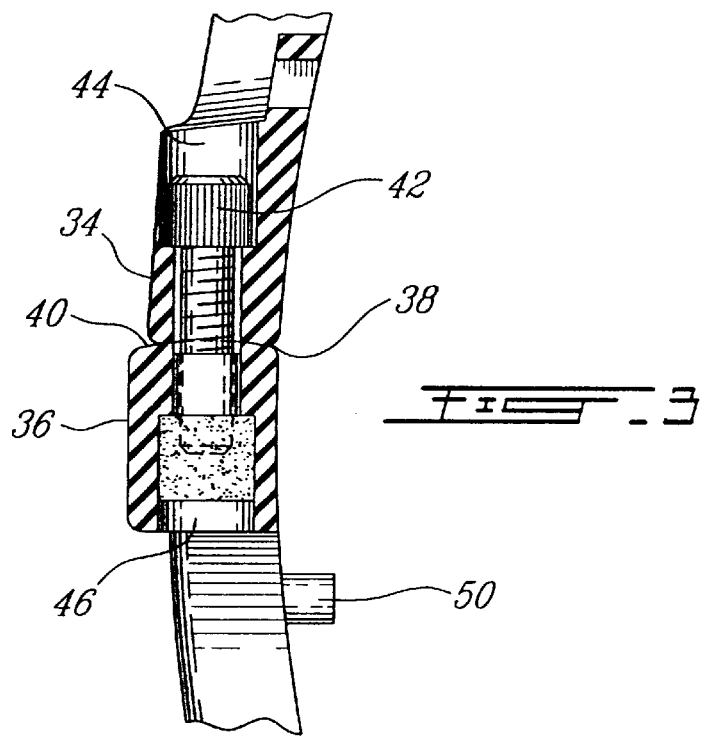
FIG. 3 is a cross-sectional view taken along lines 3—3 of FIG. 1.

As can also be seen in FIG. 2, the upper bridge part 34 has a curved lower gap face 38 while the lower bridge part has a curved upper gap face 40, the curvatures of both gap faces being complementary. Furthermore, as can be seen in FIG. 3, the gap faces 38 and 40 are also curved from the front to the rear of the eyeglasses. This combination of two curvatures ensures a secured engagement whenever the gap faces are in close contact with one another.

To close or open the gap 32 of the bridge section 22, a fastening element 42 extends through a pair of aligned openings 44 and 46 respectively provided in upper and lower parts 34 and 36.

Figure 4:
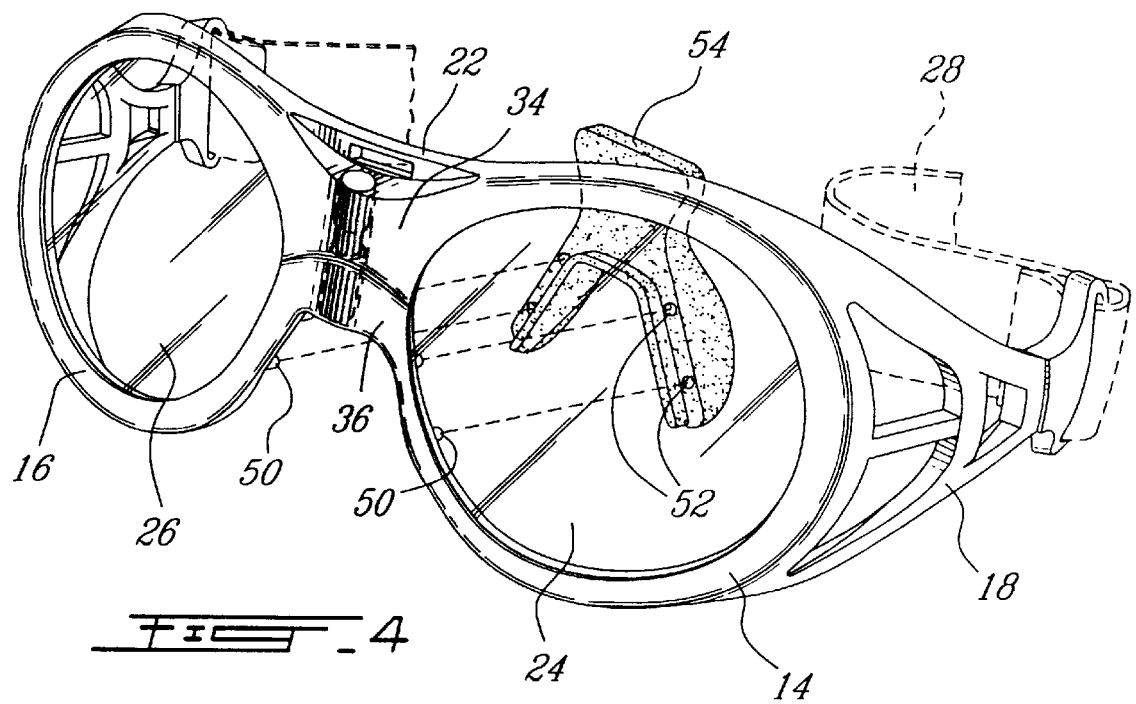
FIG. 4 is a perspective view of the eyeglasses of the present invention additionally showing a nose pad.

As can be seen in FIG. 4, a series of pins 50 are integrally formed to the lower rear face of each lens receiving section and serves to fit into a corresponding number of recesses 52 of a nose pad 54, preferably made of soft plastic material, providing a cushion effect to the eyeglass user.

Although the invention has been described above with respect to one specific form, it will be evident to the person skilled in the art that it may be refined and modified in various ways. It is therefore wished to have it understood that the present invention should not be limited in interpretation except by the terms of the following claims.

What is claimed is:

1. Eyeglasses having removable lenses comprising:
   a) a one piece plastic molded frame including:
      i) a pair of lens receiving sections, each having a lens retaining means formed therein;
      ii) a pair of opposite temple sections extending to a respective side of said lens receiving sections;
      iii) a central bridge section integral with said lens receiving sections; said bridge section being split to define an upper bridge part and a lower bridge part; said upper and lower bridge parts capable of being manually distanced from one another to define a gap and to allow lenses to be mounted in the lens retaining means of said lens receiving sections; and
   b) means engaging said upper and lower bridge parts to close said gap and to fixedly retain said lenses in said lens receiving sections.

2. Eyeglasses as defined in claim 1, wherein said engaging means comprises a fastener means extending through openings in said upper and lower bridge parts.

3. Eyeglasses as defined in claim 1, wherein said upper bridge part defines a lower gap face and said lower bridge part defines an upper gap face; both said gap faces being complementary in shape to mate when said fastening means close said gap.

4. Eyeglasses as defined in claim 3, wherein said gap faces are curved in a lateral direction from one lens receiving section to the other lens receiving section.

5. Eyeglasses as defined in claim 4, wherein said gap faces are curved in a front to rear direction.

6. Eyeglasses as defined in claim 1, wherein said lens receiving sections are provided on a rear face thereof with means for mounting a nose pad to said eyeglasses.

7. Eyeglasses as defined in claim 6, wherein said mounting means on said rear face of said lens receiving sections comprise a series of pins integrally formed to the lens receiving sections.

8. Eyeglasses having removable lenses, comprising:

a plastic molded frame, the plastic molded frame comprising:
   a pair of lens receiving sections, wherein each of the lens receiving sections is configured to retain an eyeglass lens during use;
   a pair of opposite temple sections extending to a respective side of said lens receiving sections; and
   a central bridge section coupled to said lens receiving sections, said bridge section comprising an upper bridge part and a lower bridge part, wherein said upper and lower bridge parts are movable with respect to each other to allow eyeglass lenses to be mounted within the lens receiving sections; and a fastening system coupled to said upper and lower bridge parts, wherein said fastening system is configured to inhibit movement of said upper and lower bridge parts with respect to each other.

9. Eyeglasses as defined in claim 8, wherein said fastening system comprises a fastener extending through openings in said upper and lower bridge parts.

10. Eyeglasses as defined in claim 8, wherein said upper bridge part defines a lower gap face and said lower bridge part defines an upper gap face; both said gap faces being complementary in shape to mate when moved toward each other.

11. Eyeglasses as defined in claim 10, wherein said gap faces are curved in a lateral direction from one lens receiving section to the other lens receiving section.

12. Eyeglass lenses as defined in claim 11, wherein said gap faces are curved in a front to rear direction.

13. Eyeglass lenses as defined in claim 8, wherein said lens receiving sections are configured to couple with nose pad.

14. Eyeglass lenses as defined in claim 13, wherein said lens receiving sections comprise at least one pin configured to interact with a complementary indentation of the nose pad.

* * * * *